United States Patent
Rohl et al.

(10) Patent No.: US 11,426,196 B2
(45) Date of Patent: Aug. 30, 2022

(54) ILLUMINABLE NEEDLE DEVICES, SYSTEMS, AND METHODS

(71) Applicants: BOSTON SCIENTIFIC SCIMED, INC., Maple Grove, MN (US); MAYO FOUNDATION FOR MEDICAL EDUCATION AND RESEARCH, Rochester, MN (US)

(72) Inventors: James P. Rohl, Prescott, WI (US); Craig M. Wilson, Minneapolis, MN (US); Benn Horrisberger, Blaine, MN (US); Carl W. Bauer, Roseville, MN (US); Lance A. Freeseman, Greenfield, MN (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 884 days.

(21) Appl. No.: 16/313,396

(22) PCT Filed: Dec. 16, 2016

(86) PCT No.: PCT/US2016/067262
§ 371 (c)(1),
(2) Date: Dec. 26, 2018

(87) PCT Pub. No.: WO2017/106706
PCT Pub. Date: Jun. 22, 2017

(65) Prior Publication Data
US 2019/0159805 A1    May 30, 2019

Related U.S. Application Data (60) Provisional application No. 62/269,441, filed on Dec. 18, 2015.

(51) Int. Cl.
*A61B 17/34* (2006.01)
*A61B 34/20* (2016.01)
(Continued)

(52) U.S. Cl.
CPC ...... *A61B 17/3403* (2013.01); *A61B 17/3478* (2013.01); *A61B 34/20* (2016.02);
(Continued)

(58) Field of Classification Search
CPC . A61B 17/3403; A61B 90/00; A61B 17/3478; A61B 34/20; A61B 90/30;
(Continued)

(56) References Cited

U.S. PATENT DOCUMENTS 6,584,335 B1 *  6/2003  Haar ............... A61B 5/14532
                                                        600/322
9,526,426 B1 * 12/2016  Lim ................ A61B 5/6858
(Continued)

FOREIGN PATENT DOCUMENTS

WO      9531926 A1    11/1995
WO   2011156782 A1    12/2011

OTHER PUBLICATIONS

International Search Report and Written Opinion dated Apr. 4, 2017 for International Application No. PCT/US2016/067262.
(Continued)

*Primary Examiner* — Hien N Nguyen
(74) *Attorney, Agent, or Firm* — Seager, Tufte & Wickhem, LLP (57) ABSTRACT

An illuminated needle device for performing a heart valve repair includes an outer member and an inner member. The outer member includes a body that has a proximal end and a distal end. The body of the outer member defines a lumen therethrough and the distal end of the body includes a needle. The inner member is slidably disposed within the lumen of the outer member. The inner member includes a distal end that has a radiation emitting element. The illuminated needle device is characterized by the outer and inner members together forming a flexible, elongate shaft, and the
(Continued)

inner member being configured to emit radiation from the radiation emitting element from a location proximate to the distal end of the outer member.

19 Claims, 4 Drawing Sheets

(51) Int. Cl.
*A61B 90/30* (2016.01)
*A61B 90/00* (2016.01)
*A61B 1/313* (2006.01)
*A61B 6/12* (2006.01)
*A61B 17/00* (2006.01)
*A61B 17/06* (2006.01)

(52) U.S. Cl.
CPC .............. *A61B 90/00* (2016.02); *A61B 90/30* (2016.02); *A61B 1/3137* (2013.01); *A61B 6/12* (2013.01); *A61B 90/361* (2016.02); *A61B 2017/00243* (2013.01); *A61B 2017/00783* (2013.01); *A61B 2017/06095* (2013.01); *A61B 2017/3413* (2013.01); *A61B 2034/2055* (2016.02); *A61B 2090/067* (2016.02); *A61B 2090/0811* (2016.02); *A61B 2090/306* (2016.02); *A61B 2090/309* (2016.02); *A61B 2090/3782* (2016.02)

(58) Field of Classification Search
CPC ........ A61B 90/361; A61B 2017/06095; A61B 2090/0811; A61B 2017/00783; A61B 2090/067; A61B 2090/3782; A61B 2034/2055; A61B 1/3137; A61B 2090/306; A61B 2090/309; A61B 2017/3413; A61B 6/12; A61B 2017/00243
See application file for complete search history.

(56) References Cited

U.S. PATENT DOCUMENTS

| | | |
|---|---|---|
| 2004/0225305 A1 | 11/2004 | Ewers et al. |
| 2012/0088968 A1 | 4/2012 | Ganbhir et al. |
| 2014/0171788 A1 | 6/2014 | Stigall |
| 2014/0235954 A1 | 8/2014 | Mohajer-Shojaee |
| 2014/0257136 A1 | 9/2014 | Leahy et al. |
| 2015/0182740 A1* | 7/2015 | Mickelsen ............ A61B 5/4833 604/506 |
| 2015/0209106 A1* | 7/2015 | Sliwa ................. A61B 18/1492 600/477 |
| 2016/0100797 A1* | 4/2016 | Mahapatra ............... A61B 5/03 600/301 |

OTHER PUBLICATIONS

International Preliminary Report on Patentability dated Jun. 28, 2018 for International Application No. PCT/US2016/067262.

* cited by examiner

ILLUMINABLE NEEDLE DEVICES, SYSTEMS, AND METHODS

CROSS-REFERENCE TO RELATED APPLICATIONS

This application is a National Stage of International Application No. PCT/US2016/067262, filed Dec. 16, 2016, which claims the benefit of priority under 35 U.S.C. § 119 to U.S. Provisional Application Ser. No. 62/269,441 filed Dec. 18, 2015, the entire disclosures of which are incorporated herein by reference.

TECHNICAL FIELD

The present disclosure relates to illuminable needle devices, systems, and methods.

BACKGROUND

A tricuspid valve is the valve located between the right atrium and the right ventricle in a mammalian heart. In a normally functioning tricuspid valve, when the valve is open, blood is allowed to be pumped from the right atrium into the right ventricle. When the valve is closed, blood is blocked from passing back from the right ventricle to the right atrium. Tricuspid valve regurgitation occurs when the tricuspid valve fails to open and close properly such that blood is allowed to flow backwards from the right ventricle to the right atrium of the heart.

Tricuspid valve regurgitation can be treated by an annular reduction repair procedure that can be performed using open heart surgery. During the surgery, the physician can open the right atrium to gain access to the coronary sinus, annulus and posterior leaflet. A standard "serpentine" stitch may be started at the coronary sinus ostium and stitched through the annulus around the posterior leaflet. After placing the stitch, it can be drawn tight to perform the reduction. In the current practice, annular reduction procedures can require placing patients on cardiopulmonary bypass, which involves stopping the heart and using an artificial pump to bypass the heart and lungs. The bypass procedures are associated with risks and recovery time that can deter surgeons from performing this procedure on certain patients. Accordingly, there is a need for devices and methods for performing tricuspid valve regurgitation repair using minimally invasive catheter based procedures to reduce patient recovery time and patient-risk.

SUMMARY

Disclosed herein are various embodiments of illuminable needle devices, systems, and methods. This document provides devices, systems, and methods for facile and reliable visualization of a flexible needle during a minimally invasive catheter based procedure. Various embodiments of the devices and system provided herein can include a flexible illuminable needle catheter device for accessing anatomical targets in a percutaneous transluminal medical procedure.

In Example 1, an illuminated needle device includes an outer member and an inner member. The outer member includes a body that has a proximal end and a distal end. The body of the outer member defines a lumen therethrough and the distal end of the body includes a needle. The inner member is slidably disposed within the lumen of the outer member. The inner member includes a distal end that includes a radiation emitting element. The device is characterized by the outer and inner members together forming a flexible, elongate shaft, and the inner member being configured to emit radiation from the radiation emitting element near the distal end of the outer member such that an intensity of the radiation is detectable by a receiver.

In Example 2, the device of Example 1, wherein a length and outer profile of the shaft are sized for percutaneous transluminal delivery to a patient's heart.

In Example 3, the device of Example 1 or Example 2, wherein a minimum length of the shaft is about 45.7 cm (about 18 inches).

In Example 4, the device of any one of Examples 1-3, wherein the needle has a size that ranges from about 1.07 mm (19 gauge) to about 1.47 mm (17 gauge).

In Example 5, the device of any one of Examples 1-4, wherein the device is configured to emit radiation when the distal end of the inner member is positioned flush with the distal end of the outer member.

In Example 6, the device any one of Examples 1-5, wherein the shaft has a minimum bend radius of about 10 millimeters.

In Example 7, the device of any one of Examples 1-6, the device further including a handle that has an intensity adjuster configured for allowing a user to change the intensity of the radiation.

In Example 8, the device of any one of Examples 1-7, wherein the shaft of the outer member defines a plurality of apertures.

In Example 9, the device of Example 8, wherein each aperture defines an elongate opening that partially extends in a circumferential direction about a portion of the shaft of the outer member.

In Example 10, the device of any one of Examples 1-9, wherein the outer member comprises nitinol, stainless steel, chromium cobalt, polyether ether ketone (PEEK), a polycarbonate, a polyimide, a nylon, or acrylonitrile butadiene styrene (ABS), or a combination thereof.

In Example 11, the device of any one of Examples 1-10, wherein the radiation emitting element of the inner member is radially-facing.

In Example 12, the device of any one of Examples 1-11, wherein the tubular body defines a lumen extending from the radially-facing distal opening to a proximal opening, and the radially-facing distal opening sized to receive an electrical wire coupled to the radiation emitting element, forming an electrical connection between a handle and the radiation emitting element.

In Example 13, the device of any one of Examples 1-12, wherein the inner member has a tissue-penetrating tip.

In Example 14, the device of any one of Examples 1-13, wherein the device is configured to emit radiation when the distal end of the inner member is advanced distal to the distal end of the outer member.

In Example 15, an illuminable needle system that includes the illuminable needle device of any one of Examples 1-14, and a visualization device that contains the receiver adapted to form an image of a tissue region and receive information corresponding to light intensity. The system is characterized by the inner member being configured to emit radiation from the radiation emitting element from a location proximate to the distal end of the outer member such that an intensity of the radiation is detectable by the receiver located at a minimum predetermined distance from the distal end of the outer member.

In Example 16, the device of Example 15, wherein the radiation emitting element emits a red light, blue light, purple light, green light, orange light, or a combination thereof.

In Example 17, the system of Example 15 or Example 16, wherein the receiver is an optical receiver.

In Example 18, the system of any one of Examples 15-17, wherein the receiver is an ultrasound receiver.

In Example 19, the system of any one of Examples 15-18, wherein the receiver is adapted to detect x-ray, visible light, UV, or IR electromagnetic radiation.

In Example 20, a method of penetrating tissue includes penetrating tissue using a visualization device and an illuminable needle device. The visualization device includes a receiver adapted to receive information corresponding to radiation intensity. The illuminable needle device includes an outer member includes a body that has a proximal end and a distal end. The body of the outer member defines a lumen therethrough and the distal end of the body includes a needle. The inner member is slidably disposed within the lumen of the outer member. The inner member includes a distal end that includes a radiation emitting element. The outer and inner members together form a flexible, elongate shaft. The inner member of the needle device system being configured to emit radiation from the radiation emitting element from a location proximate to the distal end of the outer member such that an intensity of the radiation is detectable by the receiver of the visualization device, in which the receiver is located at a minimum predetermined distance from the distal end of the outer member.

The method can also include emitting radiation from the distal end of the outer member of the illuminable needle device and detecting radiation intensity data from the receiver located at a minimum predetermined distance from the distal end of the outer member of the illuminable needle device.

In Example 21, a method of visualizing a surgical device includes emitting radiation from a distal end of an outer member of an illuminable needle device. The outer member of the illuminable needle device includes a body that has a proximal end and the distal end. The body defines a lumen therethrough and the distal end of the body includes a needle. The illuminable needle device includes an inner member slidably disposed within the lumen of the outer member. The inner member includes a distal end that has a radiation emitting element. The outer and inner members together can form a flexible, elongate shaft. The inner member can be configured to emit radiation from the radiation emitting element from a location proximate to the distal end of the outer member such that an intensity of the radiation is detectable by the receiver.

The method also includes detecting radiation intensity data from a receiver of a visualization device to determine a position of the distal end of the illuminable needle device. The receiver can be adapted to receive information corresponding to radiation intensity and be located at a minimum predetermined distance from the distal end of the outer member of the illuminable needle device.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

BRIEF DESCRIPTION OF THE DRAWINGS

FIGS. 2A-2C are perspective views of another example of an illuminable needle device.

FIGS. 3A and 3B are perspective views of another example of an illuminable needle device.

FIGS. 4A and 4B are photo images of a distal portion of an exemplary illuminable needle device.

While the devices and system provided herein are amenable to various modifications and alternative forms, specific embodiments have been shown by way of example in the drawings and are described in detail below. The intention, however, is not to limit the present disclosure to the particular embodiments described. On the contrary, the present disclosure is intended to cover all modifications, equivalents, and alternatives falling within the scope of the disclosure as defined by the appended claims.

DETAILED DESCRIPTION

Figure 1:
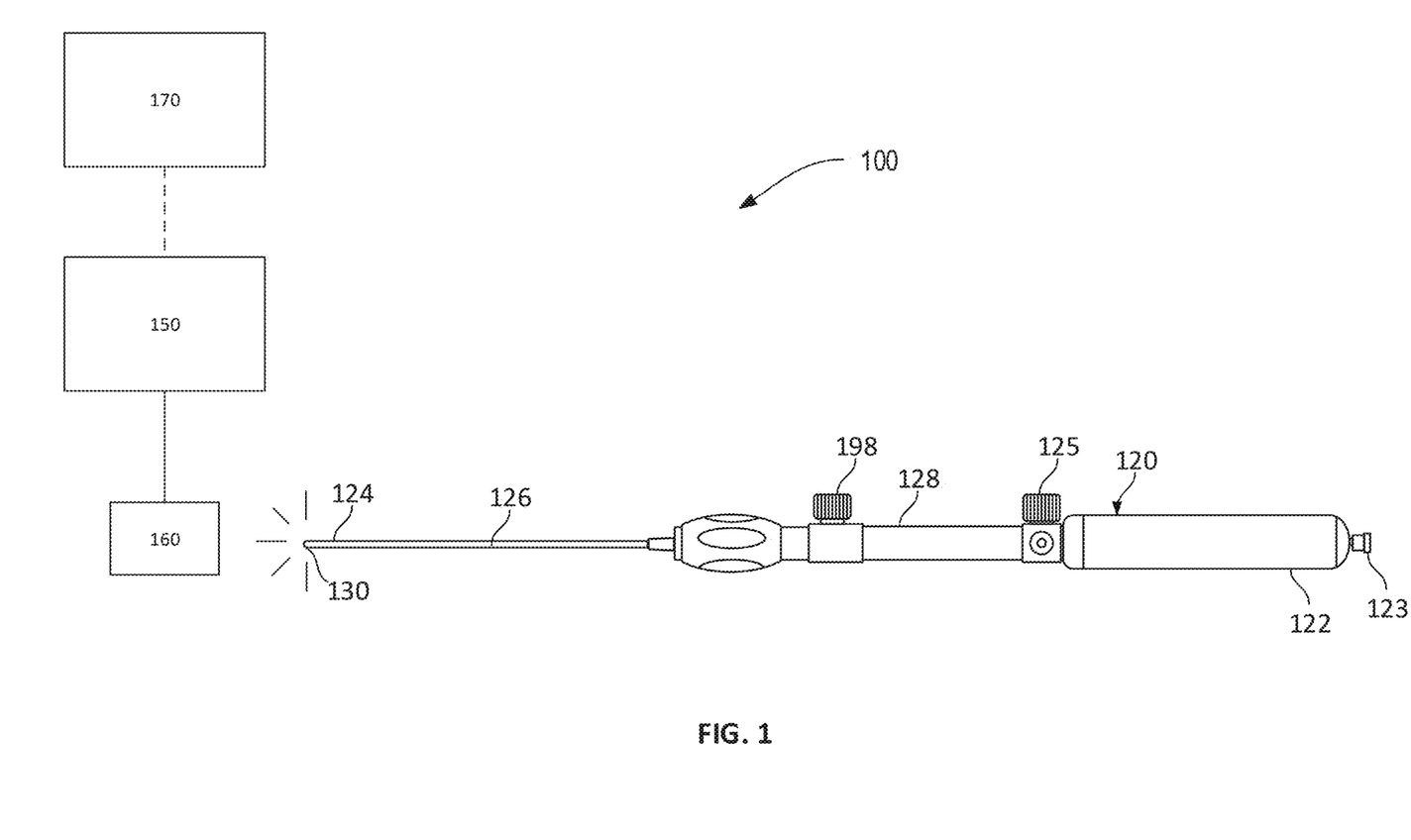
FIG. 1 is a side view of a system 100 that includes an illuminable needle device for penetrating tissue in a minimally invasive medical procedure.

Referring to FIG. 1, some embodiments of a system 100 provided herein can be used for penetrating tissue in a minimally invasive catheter-based procedure, such as a percutaneous transluminal procedure for repairing a heart valve (e.g., a tricuspid heart valve or mitral heart valve). In particular, certain embodiments of the system 100 can be used to perform a reduction of a heart valve (e.g., stitching together portions of the heart valve tissue) during a heart valve repair procedure by using a minimally invasive approach. Various embodiments of the system 100 provided herein can include an illuminable needle device 120, a visualization device 150 (e.g., a radiation-detecting device) and components relating thereto, and introducer assembly for introducing the illuminable needle system.

The illuminable needle system 100, in the depicted embodiment, can include the illuminable needle device 120 having a proximal end 122, a distal end 124, and an elongate, flexible shaft 126 between the proximal and distal ends 122, 124. The depicted embodiment of the device 120 includes a handle 128 at the proximal end 122 of the device 120 and an illuminable needle tip 130 at the distal end 124 of the device 120 for visibly penetrating tissue during a minimally-invasive surgical procedure (e.g., a tricuspid valve repair procedure). In some cases, during the heart valve repair procedure, an illuminable needle device 120 (e.g., catheter) may be introduced into a patient's vasculature through a femoral incision (or, alternatively, through other incision sites such as a jugular or a subclavian incision). The flexibility of the shaft 126 and distal end 124 of the illuminable needle device 120 allows for a practitioner to advance the device 120 through a tortuous vasculature until the distal end 124 of the device 120 reaches a desired target site, such as the right ventricle of the heart.

Although some embodiments of the devices and systems provided herein relate to the repair procedure, a wide variety of other types of medical procedures, such as vascular percutaneous transluminal procedures or medical procedures accessing an anatomical luminal pathway (e.g., an air pathway or a gastrointestinal pathway) may be contemplated by a person of ordinary skill.

As described further below, the illuminable needle device 120 in the depicted embodiment can also be included in the system 100 along with other devices, such as the visualization device 150, to form a visualization system that provides visual feedback to a user, such as a practitioner, in a percutaneous medical procedure. The visualization device 150, for example, can be used in conjunction with the illuminable needle device 120 to provide the benefit of allow the practitioner to visualize needle penetration location and depth of the illuminable needle device 120 during the medical procedure. In some cases, the visualization device 150 includes a receiver 160, such as an optical receiver (e.g., a digital camera), or an ultrasound (US) receiver (e.g., an ultrasound probe), to provide visual feedback of needle penetration information to the practitioner. The receiver 160 may be located at a desired location along the visualization device 150. For example, in some cases, the visualization device 150 can include an elongate shaft (not shown) that has the receiver 160 located at a distal tip portion of the shaft. In some cases, the receiver (e.g., optical receiver) can be adapted for detecting the intensity of the radiation being emitted from the illuminable needle tip 130 located within a predetermined distance (e.g., less than 30 mm) from the receiver 160, or within a field of view of the receiver 160. In some cases, the receiver 160 (e.g., digital camera) can be adapted to form an image of a tissue region and receive information corresponding to light intensity from the illuminable needle device 120.

Various methods can be applied to localize a portion of the illuminable needle device 120 (e.g., the needle tip 130) during a surgical procedure of a heart valve. In some cases, visual receivers (e.g., a visual camera), or ultrasound components, such as an ultrasound transmitter and an ultrasound receiver (e.g., an ultrasound probe) can be used to localize a portion of the illuminable needle device 120 within the heart. The visual receivers may be connected to a power source and the ultrasound components may be connected to an ultrasound source. The ultrasound transmitter emits high-frequency sound waves directed to a targeted tissue region and the receiver receives reflected sound waves that can be used to characterize the targeted tissue region.

In some cases, the receiver 160 can be configured for detecting radiation (e.g., light) emanating from the tip 130 of the illuminated needle device 120 and obtaining information regarding the radiation signal, such as an intensity. In some cases, the receiver can be adapted to detect x-ray, visible light, UV, or IR electromagnetic radiation. In some cases, the receiver 160 can be configured for detecting a light intensity such that the intensity data can be transmitted to a processor 170 for analysis. In some cases, the light intensity can be analyzed and correlated to a needle location by the processor 170. In some cases, the light intensity data received by the optical receiver 160 can be transferred to the processor 170 using a software algorithm, such as commercially available software algorithm, for example, Visionscape®, or a customized software algorithm, such that light intensity data can be correlated to needle penetration depth and/or a needle location data.

The visualization device 150 can be a separate device used in conjunction with the illuminable needle device 120. Accordingly, the visualization device 150 and the illuminable needle device 120 can be separate devices containing separate electrical connections. For example, the illuminable needle device 120 can include a first electrical connection to an electrical source and the visualization device 150 include a second electrical connection to the same or different electrical source that is independent of the first electrical connection.

Certain embodiments of the illuminable needle system 100 can include an ancillary device, such as an introducer assembly (not shown) to releasably engage both the visualization device 150 and the illuminable needle device 120 during a medical procedure. In particular, some embodiments of the introducer assembly include a lumen sized for insertion and lateral displacement of the distal end 124 of the illuminable needle device 120 therein to allow for the introduction of the device 120 into a patient's body. In some cases, the introducer assembly may define a distal opening to allow the shaft 126 of the illuminable needle device 120 to advance out of the introducer assembly into an anatomical area, such as the right ventricle of the heart.

Figures 2A, 2B, 2C:
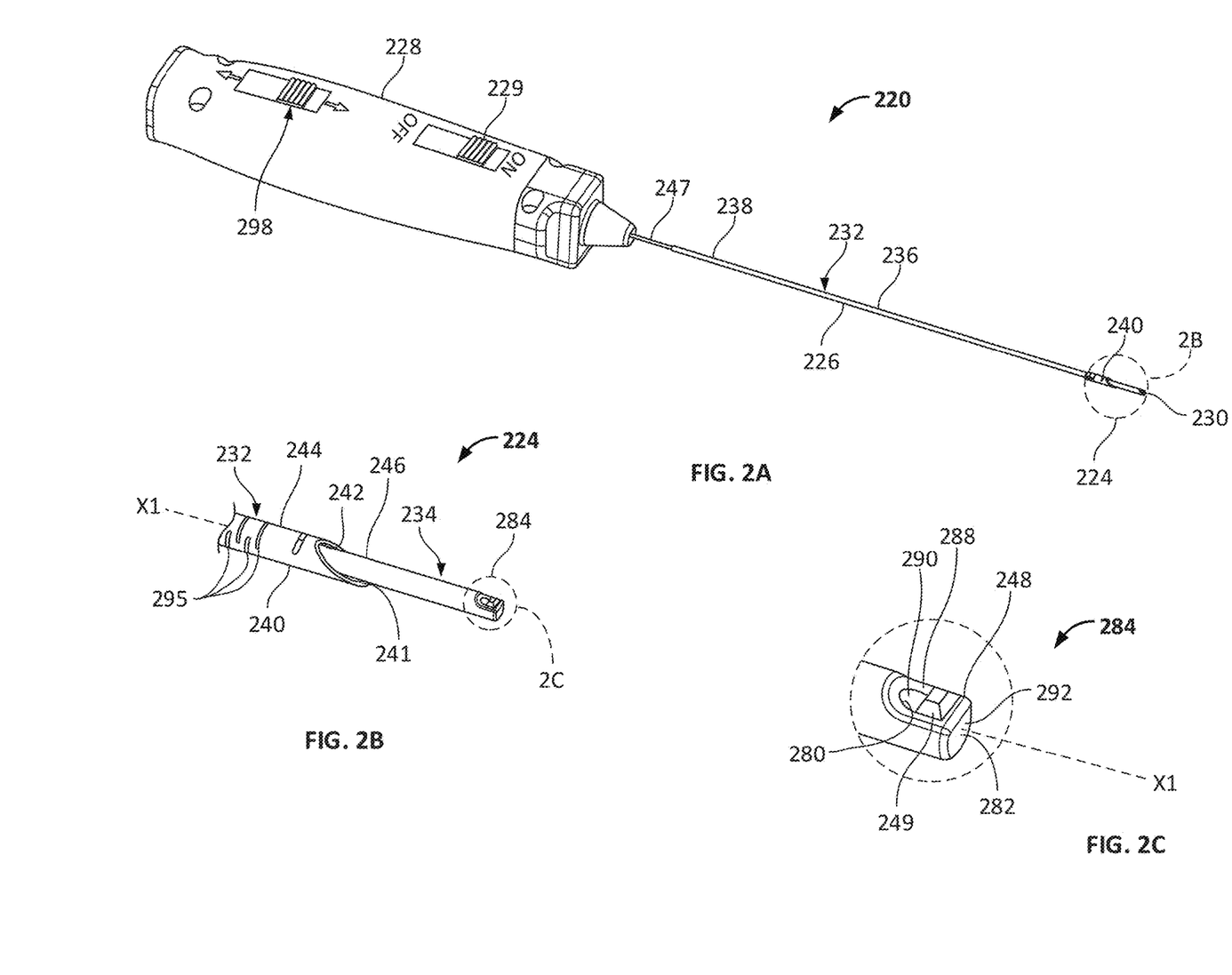
FIG. 2A shows an image of an entire device.
FIGS. 2B and 2C provide magnified detailed views of a distal portion of the illuminable needle device.

Referring to FIGS. 2A-2C, another exemplary illuminable needle device 220 includes an outer member 232 and an inner member 234. In the depicted embodiment of the illuminable needle device 220, the outer member 232 includes an elongate body 236 that has a proximal end 238 that is directly or indirectly coupleable to a handle 228 and a distal end portion 240 that includes a sharp tip (e.g., the needle 230) configured for penetrating tissue. The outer member 232 defines a lumen 242 that extends from the proximal end 238 to the distal end portion 240. The lumen 242 can be sized for receiving the inner member 234. As shown in FIG. 2B, a distal end portion 240 of outer member 232 can be beveled to create the sharp tip for penetrating tissue as the outer member 232 is axially translated in a distal direction into tissue, such as myocardium tissue. The tip's sharpness can advantageously enhance the ability of needle device 220 to tunnel through tissue during a surgical procedure. While outer member 232 can have a single-angle beveled tip, some embodiments of the outer needle designs can include other styles of sharp distal end portions, such as a bi-beveled, tri-beveled, or trocar needle tip.

Certain embodiments of the illuminable needle device 220 provided herein can include a device 220 configured for various medical procedures (e.g., a percutaneous transluminal procedure for repairing a mammalian heart valve). In some cases, the device can be sized such that its length and outer profile can be delivered to a mammalian heart using a percutaneous transluminal procedure. The length and profile of the illuminable needle device 220 is scalable to a range of sizes. A suitable length of the illuminable needle device 220, or components thereof (e.g., the outer member 232, inner member 234, or both) can range from about 38 centimeters (cm) to about 254 cm (about 15 inches to 100 inches), e.g., from about 38 cm to about 51 cm, from about 51 cm to about 102 cm, from about 102 cm to about 153 cm, from about 153 cm to about 203 cm, or from about 203 cm to about 254 cm (e.g., from about 15 inches to about 20 inches, from about 20 inches to about 40 inches, from about 40 inches to about 60 inches, from about 60 inches to about 80 inches, or from about 80 inches to about 100 inches). In some cases, the outer and inner members 232, 234 can each have a length of about 45.7 cm, or about 18 inches. A suitable profile (outer diameter) of the outer member 232 can range from about 1 millimeter (mm) to about 4 mm (about 0.04 inches to about 0.16 inches), e.g., from about 1 mm to about 2 mm, from about 2 mm to about 3 mm, or from about 3 mm to about 4 mm (e.g., from about 0.04 inches to about 0.08 inches, from about 0.08 inches to about 0.12 inches, or from about 0.12 inches to about 0.16 inches).

The size of the outer member 232 and/or needle 230 can be scalable to a range of sizes. For example, in some cases, a 1.47 mm (17-gauge) hypotube, or a 1.07 mm (19-gauge) hypotube can be used to make the outer member 232 or needle 230. In some cases, the size of the outer member 232 or needle 230 can range from about 1.47 mm (17 gauge) to about 0.41 mm (27 gauge). For example, the needle size can be about 1.47 mm (17 gauge), 1.27 mm (18 gauge), 0.91 mm (20 gauge), 0.81 mm (21 gauge), 0.71 mm (22 gauge), 0.51 mm (25-gauge), or 0.41 mm (27-gauge). In some cases, the outer member 232 and/or needle 230 can be larger than 1.47 mm (17 gauge), or smaller than 0.41 mm (27-gauge). In some cases, the outer member 232 and/or needle 230 can be made with various wall thicknesses. For example, in some cases, the needle 230, or the outer member 232, can have a wall thickness ranging from about 0.05 mm to about 0.2 mm, or from about 0.002 inches to about 0.006 inches. The needle 230, or the outer member 232, may be manufactured by using various metal drawing processes, such as bar drawing, wire drawing, tube drawing, or a combination thereof.

The inner member 234 of the illuminable needle device 220, best shown in FIGS. 2B and 2C, is sized to slidably move distally, or proximally, within the lumen 242 of the outer member 232. The inner member 234 can have an elongate body 246 that includes a proximal end 247 (FIG. 2A) and a distal end 248 (FIG. 2C). In some cases, the inner member 234 can include a generally tubular body 246. The distal end 248 of the inner member 234, in some cases, can include one or more radiation emitting element 249. The inner member 234 can be configured to emit radiation from the radiation emitting element 249 at the distal end portion 240 of the outer member 232 such that an intensity of the radiation is detectable by a receiver (e.g., the receiver 160 of FIG. 1). In some cases, radiation emitting element 249 can include a light-emitting element, such as a LED or an optical fiber (see optical fiber 349 of FIG. 3B). In some cases, the inner member 234 includes a distal end portion 284 including a plurality of radiation emitting elements 249 aligned longitudinally along the distal end portion 284.

The inner member 234 can include a lumen 280 therethrough its body 246. A source of radiation can be arranged at the distal tip/the radiation emitting element 249 or can be arranged proximally and connected to the radiation emitting element 249 by guiding means. For example, the guiding means can include the lumen 280 sized to receive at least one electrical connector (not shown) (e.g., an electrical wire), which is configured to provide an electrical connection between the handle 228 and the radiation emitting element 249 (e.g., a LED or a laser diode). The handle 228 can be connectable to a power source such as a battery, or a power-supply outlet, by a power-supply connector (see power-supply connector 123 of FIG. 1). The handle can optionally include an on-off switch 229 to emit radiation from the radiation emitting element 249, as desired. In some cases, the inner member 234 can be removed from the lumen 242 of the outer member 232 completely by proximally retracting the inner member 234 and pulling the inner member 234 out from the proximal end 238 of the outer member 232.

Referring to FIG. 2C, the distal end portion 284 of the inner member 234 can include a reduced profile configured for securing and positioning the radiation emitting element 249. For example, as shown, the inner member 234 can include tubular body having a semi-cylindrical end portion having a semi-circular cross-section at its distal end portion 284. A distal most end 282 of the inner member 234 may be positioned flush with a distal most end 241 of the outer member 232 to emit radiation (e.g., light) from the needle 230 of the illuminable needle device 220. In some cases, the distal most end 282 of the inner member 234 may be positioned proximal to the distal most end 241 of the outer member 232 to emit radiation from the needle lumen 242. For example, in some cases, the inner member's distal end 248 may be proximally positioned about 0.25 mm, about 0.5 mm, about 1 mm, about 2 mm, about 3 mm, about 4 mm, or about 5 mm from the distal most end 241 of the outer member 232 to emit detectable radiation from the needle 230. In some cases, the inner member 234 and/or the outer member 232 may contain a stop feature (not shown) to prevent the inner member 234 from extending beyond the outer member's distal most end 241. For example, in some cases, the outer member 232 can include reduced luminal diameter (e.g., a tapered or stepped luminal surface) and/or the inner member 234 can include a radial protrusion (not shown) for engaging with the outer member 232.

As shown in FIG. 2C, the distal end portion 284 of the inner member 234 can include a distal surface 288 that defines an opening 290 and orients the radiation emitting element 249 (e.g., LED). The distal surface 288 can be shaped to facilitate seating of a surface of the radiation emitting element 249 at the distal end portion 284 of the inner member 234. In some cases, the inner member 234 can include a tubular body defining a radially-facing distal opening 290 disposed on a planar surface parallel to a central axis of the semi-cylindrical distal portion, in which the planar surface is configured to receive the radiation emitting element 249. In some cases, the distal surface 288 can include a surface contour that is complementary of a surface contour of the radiation emitting element 249. For example, in some cases, the distal surface 288 can include a planar surface, or a curved surface. In some cases, the distal surface 288 can be parallel to a central axis "X1" of the inner member 234. In some cases, the distal surface 288 can be configured to orient the radiation emitting element 249 at the distal end portion 284 of the inner member 234 such that radiation emitted from the element 249 in a radial direction. A radially-directed radiation emitting element 249 can be oriented to emit radiation from the beveled opening of the outer member 232 when the inner member's distal most end 282 is positioned flush with, or proximately located near the outer member's distal most end 241, to maximize intensity of the radially-directed radiation being emitted by the illuminable needle device 220. A radially-directed radiation emitting element 249 can be advantageous for visualization systems in which a receiver (e.g., the receiver 160 of FIG. 1) is peripherally located to the distal end portion 284 of the illuminable needle device 220. In some cases, the inner member 234 can include one or more radiation emitting element 249 connected to an axial face 292 of a distal most end 282 of the inner member 234. An axial-directed radiation emitting element 249 can be beneficial in visualization systems in which the receiver is located at a location axial to the distal end portion 240 of the illuminable needle device 220.

Some embodiments of the inner member 234 can include a distal end portion 284 having one of a variety of tip configurations. In some cases, the distal end portion 284 can be blunt or rounded. In some cases, the distal end portion 284 can be shaped for penetrating or piercing tissue, for example, a needle. The inner member 234 that includes the tissue penetrating tip may be distally advanced relative to the outer member 232 when the illuminable needle device 220 is penetrating or piercing tissue.

The shaft 226 of the illuminable needle device 220 can be configured, in various cases, with adequate flexibility for maneuvering within a torturous vascular pathway. In some cases, the shaft 226 (which includes the outer and inner members assembled together) can have a bend radius that ranges from about 2 mm to about 50 mm (e.g., from about 2 mm to about 5 mm, from about 5 mm to about 10 mm, from about 10 mm to about 20 mm, from about 20 mm to about 30 mm, from about 30 mm to about 40 mm, or from about 40 mm to about 50 mm). In some cases, the shaft 226 can have a to bend radius of about 2 mm, about 5 mm, about 7 mm, about 10 mm, about 15 mm, about 20 mm, about 30 mm, or about 50 mm. In some cases, the shaft 226 can include a minimum bending radius of about 2 mm, about 5 mm, about 10 mm, about 15 mm, about 20 mm, about 25 mm, about 30 mm, about 35 mm, about 40 mm, about 45 mm, or about 50 mm. The flexible shaft can provide the benefits of facilitating facile delivery and maneuverability of the illuminable needle device 220 when the device 220 is used to access anatomical targets, such as the right ventricle of the heart, during a percutaneous transluminal procedure.

Still referring to FIGS. 2A-2C, the needle device 220 includes a wavelength adjustment feature 298 (see also features 198, 398 of FIGS. 1 and 3A) configured for allowing a user to change wavelength of electromagnetic radiation (e.g., light) emitted by the light emitting element 249. The wavelength adjustment feature 298 can be included in the handle 228 of the illuminable needle device 220. In some cases, the illuminating needle device 220 can emit electromagnetic radiation in the visible light spectrum (i.e. visible light) that includes a wavelength range from about 390 nanometers to about 700 nanometers, or a frequency range of about 430 THz to about 770 THz. For example, the illuminating needle device 220 may transmit light with a spectral color that includes, but is not limited to, violet, blue, green, yellow, orange, red, and combinations thereof. In some cases, the illuminating needle device 220 can emit radiation in the infrared (IR) spectral region. In some cases, the illuminating needle device 220 can emit x-rays, i.e., electromagnetic waves with a wavelength less than about $10^{-9}$ meters.

The illuminable needle device 220 provided herein can include a radiation (e.g., light) intensity adjuster (see adjuster 125 of FIG. 1) configured for allowing a user, such as a medical practitioner, to change the intensity of the radiation (e.g., light) emanating from the radiation emitting element 249. In some cases, the radiation intensity adjuster can be included in the handle 228 of the needle device 220. For example, in the some cases, the radiation intensity adjuster can include, but is not limited to, a scroll-based switch that includes a scroll wheel, and a depressible (or slidable) multi-settable switch configured to allow the user to adjust the radiation intensity, as desired. The radiation intensity adjuster can provide a benefit of allowing the user to adjust the radiation intensity to improve (e.g., optimize), as desired, detectability of the radiation. In some cases, the radiation intensity adjuster may be adjusted to decrease, or increase, the intensity of the radiation emitted from the radiation emitting element 249 to optimize its detectability in tissues of varying densities.

In some cases, the distal end portion 240 of the outer member 232 may include a plurality of apertures 295, as depicted in FIG. 2B, to allow radiation (e.g., light) from the radiation emitting element 249 (e.g., LED) to emanate from at least portions of the shaft 226 of the illuminable needle device 220. In some cases, a plurality of apertures 295 are arranged on the outer body 236 along a longitudinal axis (X1) defined by the outer member 232. The apertures 295 can be optionally slot-shaped. In some cases, each slot-shaped aperture 295 can be elongated circumferentially about the outer body 236. Apertures 295 along the side wall of the outer member 232 can advantageously allow a practitioner to visually detect the trajectory of the needle 230 and the depth of needle penetration. In some cases, the trajectory of the needle 230 may be determined by measuring the relative intensity values between the apertures 295 along the outer body 236. For example, a distally-located aperture may be less intense than a proximally-located aperture when the needle 230 in partially embedded in the targeted tissue. In another example, the proximally-located aperture may be less intense than a distally-located hole aperture when the needle 230 has fully pierced through tissue and emerged from a tissue surface. As such, the overall trajectory of the needle 230 may be determined by assessing the light intensities of the apertures along the body portion of the illuminable needle device 220.

In some cases, a plastic material (e.g., an epoxy) may be deposited in one or more apertures 295. The deposited plastic material (e.g., epoxy) may be doped with a colorant such that the light transmitted through each epoxied aperture emanates a desired color. In some cases, the dopant may include phosphors, quantum dots (crystals of semiconductor material), fluorescing nanoparticles, or combinations thereof.

The outer member 232 can, in some cases, contain medically-compatible metals, polymers, and/or ceramics. In some cases, the outer member 232 can include metals, such as, but not limited to, nitinol, stainless steel, chromium cobalt, or combinations thereof. In some cases, the outer member 232 can include high-strength polymers, such as polyether ether ketone (PEEK), a polycarbonate, a polyimide, a nylon, or acrylonitrile butadiene styrene (ABS). In some cases, the outer member 232 can include combinations of metal, polymer, and ceramic materials, such as a wire-braided polymer shaft, or a ceramic-filled polymer.

Figures 3A, 3B:
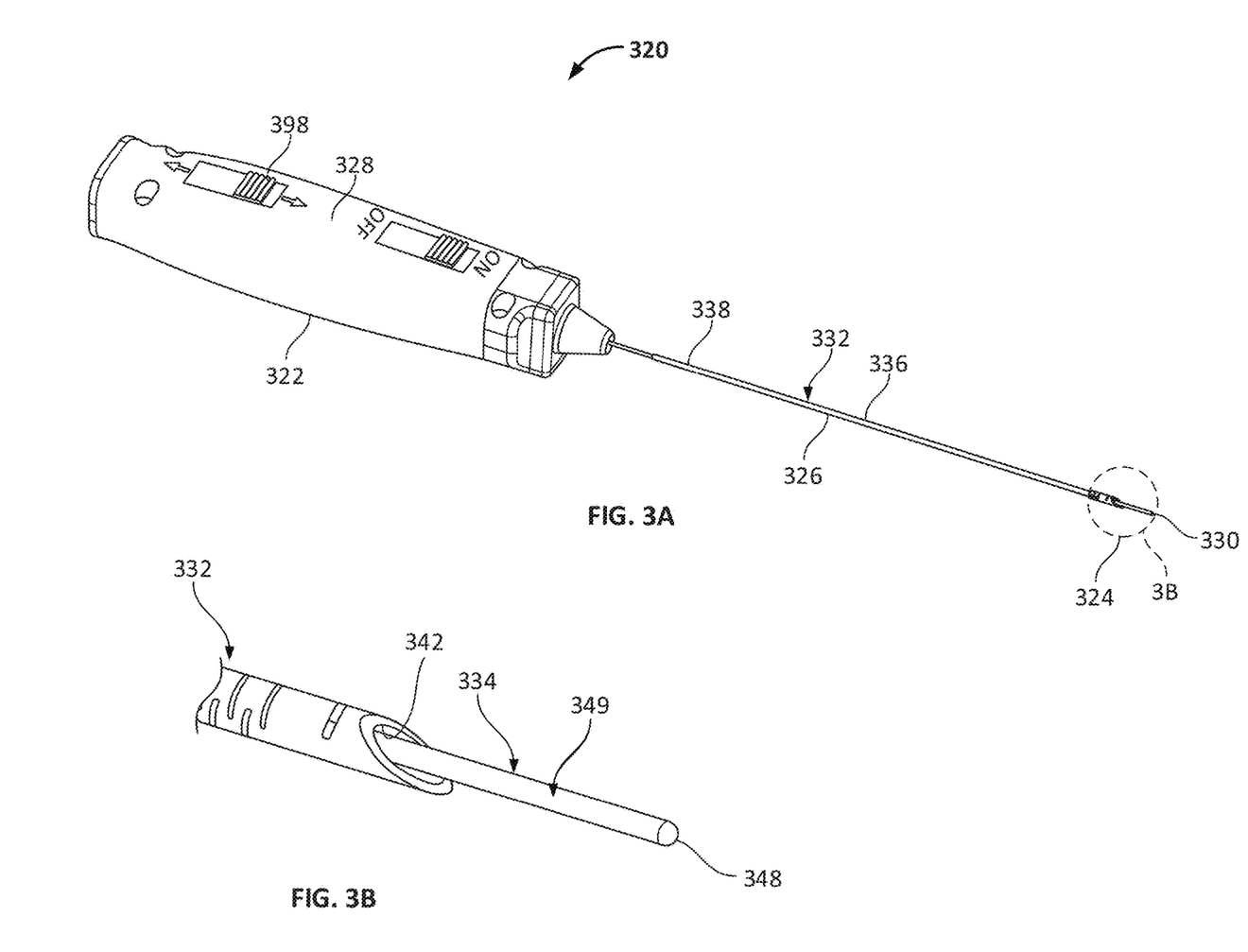
FIG. 3A shows an image of an entire device.
FIG. 3B shows a magnified detailed view of a distal portion of the illuminable needle device.

Referring to FIGS. 3A and 3B, another embodiment of an illuminable needle to device 320 provided herein includes a proximal end 322, a distal end 340, and an elongate, flexible shaft 326 between the proximal and distal ends 322, 340. The depicted embodiment of the device 320 includes a handle 328 at the proximal end 322 of the device 320 and an illuminable needle tip 330 at the distal end 340 of the device 320 for visibly penetrating tissue during a minimally-invasive medical procedure, such as a heart valve repair procedure. The shaft 326 of the depicted illuminable needle device 320 includes an outer member 332 and an inner member 334. The outer member 332 can have an elongate body 336 that includes a proximal end 338 that is directly or indirectly couplable to the handle 328. The distal end 340 can be formed into a needle tip 330 configured for penetrating tissue. The outer member 332 can define a lumen 342 extending from the proximal end 338 to the distal end 348 that is sized for receiving the inner member 334.

The inner member 334, in various embodiments of the illuminable needle device 320 provided herein, can include an optical fiber 349, as best shown in FIG. 3B. The inner member 332 of the illuminable needle device 320 can, in some cases, include multiple optical fibers 349. For example, in some cases, the inner member 334 can house two, three, four, five, six, seven, eight, nine, ten, or more than ten optical fibers 349 within its lumen 342. Some embodiments of the illuminable needle device 320 provided herein include an inner member 334 containing multiple lumens for housing multiple optical fibers 349 in separate lumens. For example, in some cases, the inner member 334 can include at least two lumens, e.g., a first lumen and a second lumen, in which the first lumen houses a first optical fiber and the second lumen houses a second optical fiber.

Figure 4A:
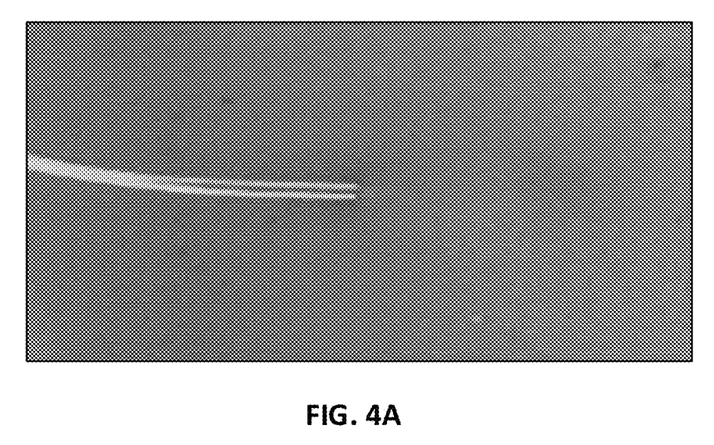
FIG. 4A shows the device in an unilluminated state.
Figure 4B:
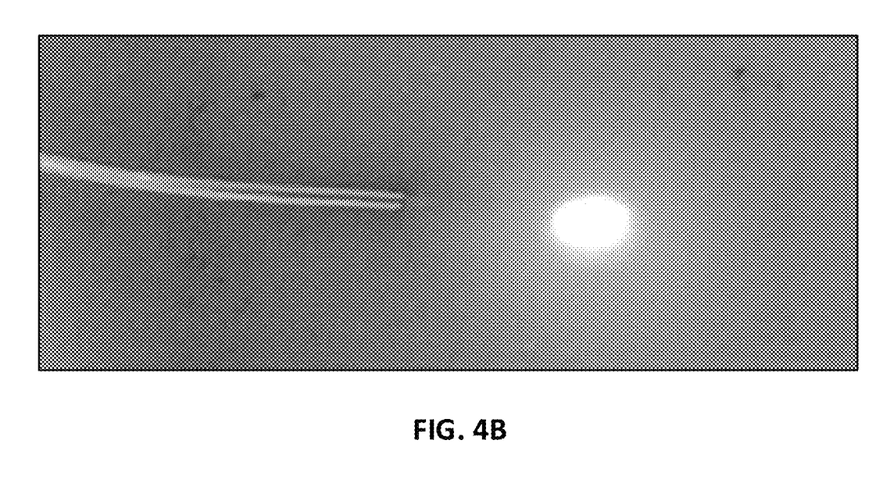
FIG. 4B shows the inner device in an illuminated state.

FIGS. 4A and 4B are images of a distal portion of exemplary illuminable needle device provided herein. The inner member is shown extended distally from an outer member, where a light emitting element is an unilluminated state in FIG. 4A and in an illuminated state in FIG. 4B.

The illuminable needle device 320 provided herein can be applied in a percutaneous transluminal procedure for repairing the heart valve (e.g., tricuspid valve). In one example, a method of penetrating tissue includes penetrating tissue using a visualization device and an illuminable needle device provided herein. The visualization device can include a receiver adapted to receive information corresponding to radiation intensity. The illuminable needle device can include an outer member includes a body that has a proximal end and a distal end. The body of to the outer member can define a lumen therethrough and the distal end of the body includes a needle. The inner member can slidably disposed within the lumen of the outer member. The inner member can include a distal end that includes a radiation emitting element. The outer and inner members can together form a flexible, elongate shaft. The inner member of the needle device system can be configured to emit radiation from the radiation emitting element from a location proximate to the distal end of the outer member such that an intensity of the radiation is detectable by the receiver of the visualization device, in which the receiver is located at a minimum predetermined distance from the distal end of the outer member.

The method can also include emitting radiation from the distal end of the outer member of the illuminable needle device and detecting radiation intensity data from the receiver located at a minimum predetermined distance from the distal end of the outer member of the illuminable needle device.

In another example, a method of visualizing a surgical device can include emitting radiation from a distal end of an outer member of an illuminable needle device. The outer member of the illuminable needle device can include a body that has a proximal end and the distal end. The body can define a lumen therethrough and the distal end of the body includes a needle. The illuminable needle device can include an inner member slidably disposed within the lumen of the outer member. The inner member can include a distal end that has a radiation emitting element. The outer and inner members together can form a flexible, elongate shaft. The inner member can be configured to emit radiation from the radiation emitting element from a location proximate to the distal end of the outer member such that an intensity of the radiation is detectable by the receiver.

The method also may include detecting radiation intensity data from a receiver of a visualization device to determine a position of the distal end of the illuminable needle device. The receiver can be adapted to receive information corresponding to radiation intensity and be located at a minimum predetermined distance from the distal end of the outer member of the illuminable needle device.

It should be understood that one or more design features of the devices provided herein can be combined with other features of other devices provided herein. In effect, hybrid designs that combine various features from two or more of the device designs provided herein can be created, and are within the scope of this disclosure.

While this specification contains many specific implementation details, these should not be construed as limitations on the scope of any disclosure or of what may be claimed, but rather as descriptions of features that may be specific to particular embodiments of particular disclosures. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

In addition to being directed to the teachings described above and claimed below, devices and/or methods having different combinations of the features described above and claimed below are contemplated. As such, the description is also directed to other devices and/or methods having any other possible combination of the dependent features claimed below.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the present disclosure, to the full extent indicated by the broad, general meaning of the terms in which the appended claims are expressed. To the extent that these various modifications do not depart from the spirit and scope of the appended claims, they are intended to be encompassed therein. All references, publications, and patents referred to herein, including the figures and drawings included therewith, are incorporated by reference in their entirety.

We claim:

1. An illuminated needle device for performing a heart valve repair, the device comprising:
    an outer member including a body that has a proximal end and a distal end, the body defining a lumen therethrough, the distal end of the body comprising a needle; and
    an inner member slidably disposed within the lumen of the outer member, the inner member including a distal end comprising a radiation emitting element;
    the outer and inner members together forming a flexible, elongate shaft configured for flexibly maneuvering within a torturous vascular pathway into the heart, and the inner member being configured to emit radiation from the radiation emitting element from a location proximate to the distal end of the outer member;
    wherein a distal end portion of the outer member defines a plurality of apertures, wherein one or more of the plurality of apertures is filled with an epoxy configured to allow radiation to pass therethrough, wherein the epoxy is doped with a colorant configured to color light transmitted through each epoxied aperture.

2. The device of claim 1, wherein a length and outer profile of the shaft are sized for percutaneous transluminal delivery to a patient's heart.

3. The device of claim 1, wherein a minimum length of the shaft is about 45.7 cm (about 18 inches).

4. The device of claim 1, wherein the needle has a size that ranges from about 1.07 mm (19 gauge) to about 1.47 mm (17 gauge).

5. The device of claim 1, wherein the device is configured to emit radiation when the distal end of the inner member is positioned flush with the distal end of the outer member.

6. The device of claim 1, wherein the shaft has a minimum bend radius of about 10 millimeters.

7. The device of claim 1, the device further comprising a handle that includes an intensity adjuster configured for allowing a user to change the intensity of the radiation.

8. The device of claim 1, wherein each aperture defines an elongate opening that partially extends in a circumferential direction about a portion of the shaft of the outer member.

9. The device of claim 1, wherein the outer member comprises nitinol, stainless steel, chromium cobalt, polyether ether ketone (PEEK), polycarbonate, polyimide, nylon, or acrylonitrile butadiene styrene (ABS), or a combination thereof.

10. The device of claim 1, wherein the radiation emitting element of the inner member is radially-facing.

11. The device of claim 10, wherein a tubular body defines a lumen extending from the radially-facing distal opening to a proximal opening, and the radially-facing distal opening sized to receive an electrical wire coupled to the radiation emitting element, forming an electrical connection between a handle and the radiation emitting element.

12. The device of claim 1, wherein the inner member has a tissue-penetrating tip.

13. The device of claim 1, wherein the device is configured to emit radiation when the distal end of the inner member is advanced distal to the distal end of the outer member.

14. An illuminable needle system comprising:
   a visualization device comprising a receiver adapted to form an image of a tissue region, the receiver receiving information corresponding to radiation intensity; and
   an illuminable needle device comprising:
      an outer member including a body that has a proximal end and a distal end, the body defining a lumen therethrough, the distal end of the body comprising a needle; and
      an inner member slidably disposed within the lumen of the outer member, the inner member including a distal end comprising a radiation emitting element;
      the outer and inner members together forming a flexible, elongate shaft configured for flexibly maneuvering within a torturous vascular pathway into the heart; and
      the inner member being configured to emit radiation from the radiation emitting element from a location proximate to the distal end of the outer member such that an indicator of the radiation intensity is detectable by the receiver;
      wherein a distal end portion of the outer member defines a plurality of apertures, wherein one or more of the plurality of apertures is filled with an epoxy configured to allow radiation to pass therethrough wherein the epoxy is doped with a colorant configured to color light transmitted through each epoxied aperture.

15. The device of claim 14, wherein the radiation emitting element emits a red light, blue light, purple light, green light, orange light, or a combination thereof.

16. The system of claim 14, wherein the receiver is an optical receiver.

17. The system of claim 14, wherein the visualization device further comprises an ultrasound transmitter and wherein the receiver is an ultrasound receiver.

18. The system of claim 14, wherein the receiver is adapted to detect x-ray, visible light, UV, or IR electromagnetic radiation.

19. A method of penetrating tissue comprising:
   penetrating tissue with an illuminable needle device comprising:
      an outer member including a body that has a proximal end and a distal end, the body defining a lumen therethrough, the distal end of the body comprising a needle;
      an inner member slidably disposed within the lumen of the outer member, the inner member including a distal end comprising a radiation emitting element;
      the outer and inner members together forming a flexible, elongate shaft configured for flexibly maneuvering within a torturous vascular pathway into the heart, wherein a distal end portion of the outer member defines a plurality of apertures, wherein one or more of the plurality of apertures is filled with an epoxy configured to allow radiation to pass therethrough, wherein the epoxy is doped with a colorant configured to color light transmitted through each epoxied aperture; and
      the inner member being configured to emit radiation from the radiation emitting element from a location proximate to the distal end of the outer member such that an intensity of the radiation is detectable by the receiver;
   emitting radiation from the distal end of the outer member of the illuminable needle device; and
   detecting radiation intensity data from a receiver of a visualization device, the receiver being adapted to receive information corresponding to radiation intensity and being located at a minimum predetermined distance from the distal end of the outer member of the illuminable needle device.

* * * * *